United States Patent [19]
Tay

[11] Patent Number: 5,984,102
[45] Date of Patent: *Nov. 16, 1999

[54] MEDICAL ELECTRODE PACKAGING TECHNOLOGY

[75] Inventor: Sew-Wah Tay, Plymouth, Minn.

[73] Assignee: SurVivaLink Corporation, Minneapolis, Minn.

[*] Notice: This patent is subject to a terminal disclaimer.

[21] Appl. No.: 09/033,294

[22] Filed: Mar. 2, 1998

Related U.S. Application Data

[60] Continuation-in-part of application No. 08/712,224, Sep. 11, 1996, Pat. No. 5,850,920, which is a division of application No. 08/411,102, Mar. 27, 1995, Pat. No. 5,579,919, which is a division of application No. 07/950,823, Sep. 24, 1992, Pat. No. 5,402,884.

[51] Int. Cl.⁶ .............................. B65D 85/86; A61N 1/39; A61B 5/0408; A61B 5/0424
[52] U.S. Cl. ........................ 206/701; 206/210; 206/438; 206/727; 206/439; 607/4; 607/5; 600/372; 600/393; 600/391
[58] Field of Search .................................. 206/207, 210, 206/438, 701, 727, 728, 439; 607/4, 5; 600/372, 393, 395, 391, 397, 394

[56] References Cited

U.S. PATENT DOCUMENTS

| | | | |
|---|---|---|---|
| 3,086,652 | 4/1963 | Lipscomb | 206/328 |
| 3,198,329 | 8/1965 | Golenpaul et al. | |
| 3,265,945 | 8/1966 | Jennings et al. | 206/328 |
| 3,585,275 | 6/1971 | Gillemot et al. | 206/328 |
| 3,602,216 | 8/1971 | Moe, Jr. | 600/397 |
| 3,685,645 | 8/1972 | Kawaguchi | 206/438 |
| 3,701,346 | 10/1972 | Patrick, Jr. et al. | 206/328 |
| 3,798,329 | 8/1965 | Golenpaul et al. | 206/65 |
| 3,805,769 | 4/1974 | Sessions | 600/391 |
| 3,830,229 | 8/1974 | Johnson | 206/328 |
| 3,834,373 | 9/1974 | Sato . | |
| 3,868,946 | 3/1975 | Hurley | 600/391 |
| 3,934,373 | 9/1974 | Sato | 600/391 |
| 3,961,623 | 6/1976 | Milani et al. | 600/397 |
| 4,029,086 | 6/1977 | Corsanti | 600/397 |
| 4,034,854 | 7/1977 | Bevilacqua | 206/210 |
| 4,040,412 | 8/1977 | Sato | 600/391 |
| 4,092,985 | 6/1978 | Kaufman | 607/152 |
| 4,423,732 | 1/1984 | Tarjan et al. | 206/438 |
| 4,439,810 | 3/1984 | Shimada et al. | 206/328 |
| 4,482,313 | 11/1984 | Repik et al. . | |
| 4,487,313 | 12/1984 | Repik et al. | 206/438 |
| 4,779,630 | 10/1988 | Scharnberg et al. | 600/397 |
| 5,402,884 | 4/1995 | Gilman et al. | 206/438 |
| 5,462,157 | 10/1995 | Freeman et al. | 206/438 |
| 5,579,919 | 12/1996 | Gilman et al. | 206/701 |
| 5,850,920 | 12/1998 | Gilman et al. | 206/701 |

FOREIGN PATENT DOCUMENTS 2483-215  6/1981  France .

*Primary Examiner*—Anthony Stashick
*Attorney, Agent, or Firm*—Patterson & Keough, P.A.

[57] ABSTRACT

The invention provides a sealed package system for housing at least two medical electrode devices and for enabling the periodic testing thereof, comprising a thin, generally flat flexible envelope constructed and arranged to form an interior cavity for enclosing a conductive gel contact surface of each of the electrode devices. A conductive liner is disposed between conductive gel contact surface of each of the electrode devices.

32 Claims, 5 Drawing Sheets

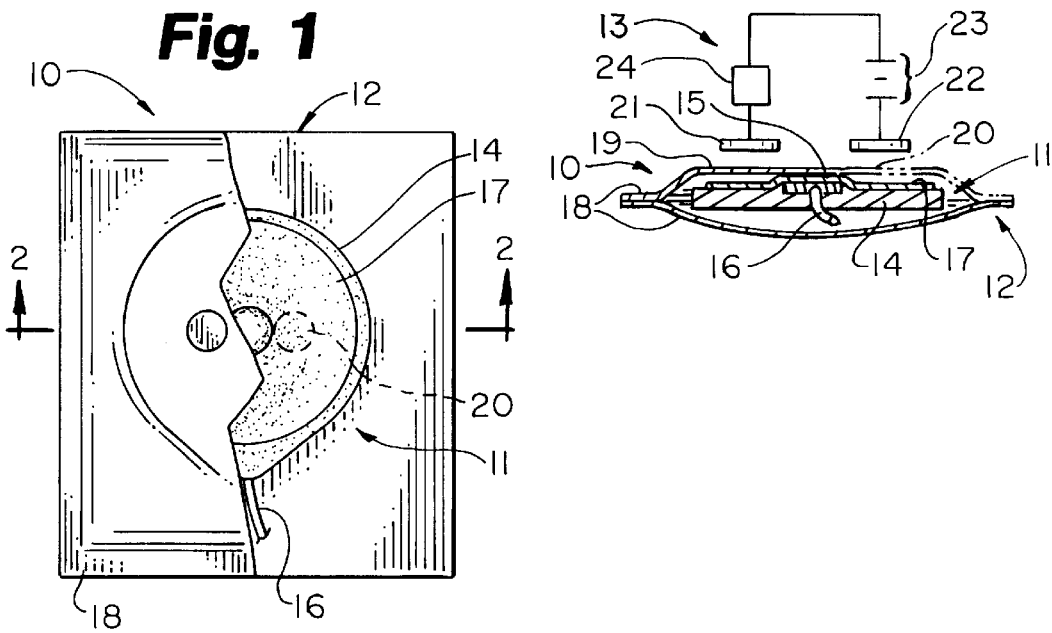
Fig. 1
Fig. 2
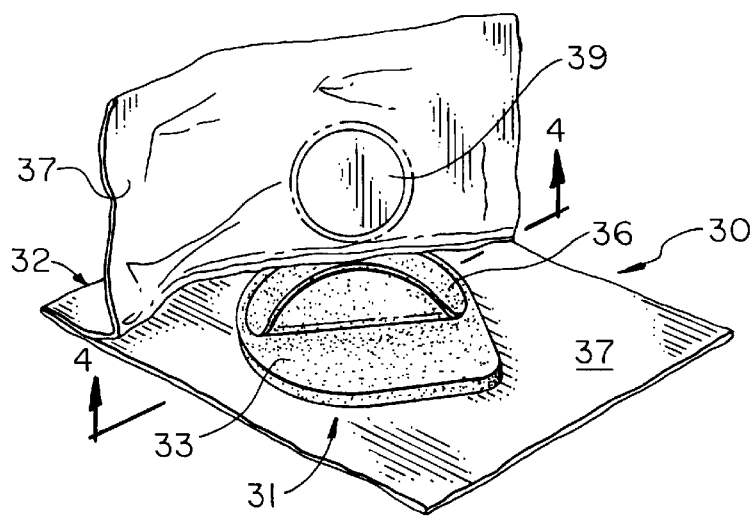
Fig. 3
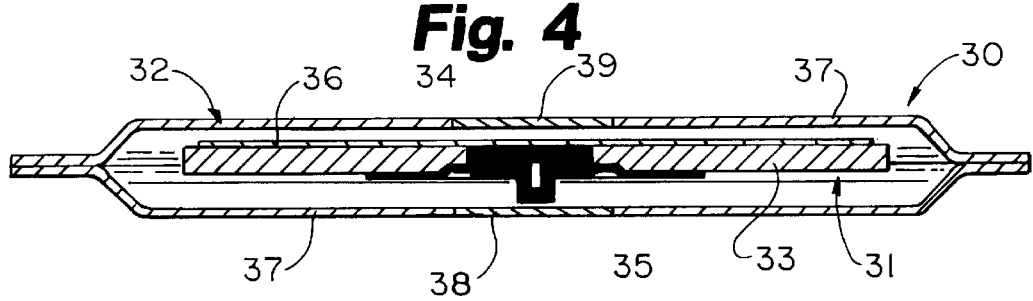
Fig. 4

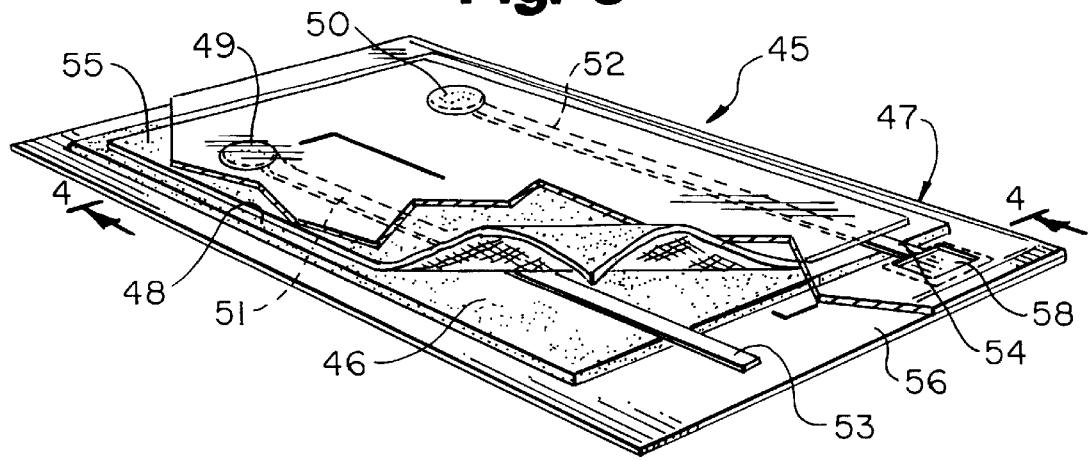
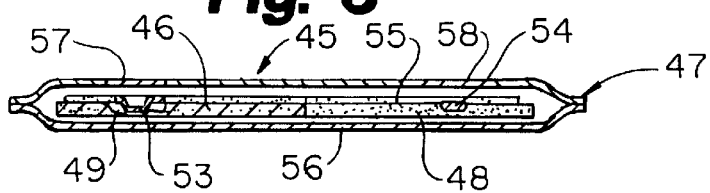
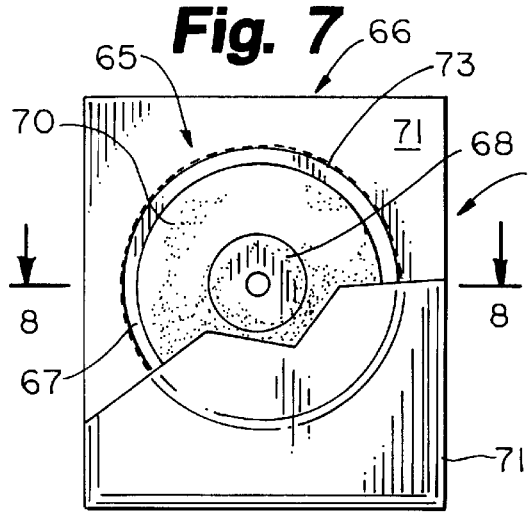
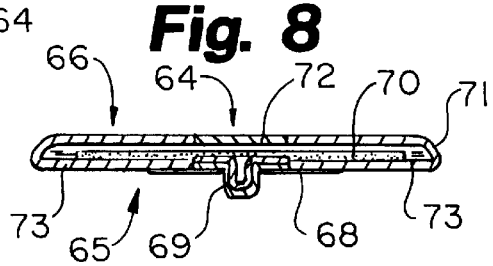

MEDICAL ELECTRODE PACKAGING TECHNOLOGY

This application is a continuation-in-part of U.S. application Ser. No. 08/712,224 filed Sep. 11, 1996 now issued U.S. Pat. No. 5,850,920 issued Dec. 22, 1998, which is a divisional application of U.S. application Ser. No. 08/411,102 filed Mar. 27, 1995, now issued as U.S. Pat. No. 5,579,919, issued Dec. 3, 1996, which is a divisional application of U.S. application Ser. No. 07/950,823, filed Sep. 24, 1992 and now issued as U.S. Pat. No. 5,402,884, issued Apr. 4, 1995.

BACKGROUND OF THE INVENTION

This invention relates to electro-medical apparatus and methods and particularly to packaging structures for medical electrode apparatus. The packaging structures are particularly useful for housing medical electrodes prior to use. And, the packaging structures have features that will allow the stored medical electrodes to be periodically tested during storage.

In the past, various electrode devices and/or methods, including packaging schemes have been used and proposed. However, these devices are generally complex, inefficient to use and have significant shortcomings. Specifically, most electrodes and packaging structures for such electrodes do not provide the ability to test for readiness after, typically, long periods of storage without compromising the sterility and performance of the electrode.

Despite the need for an electrode device and electrode packaging which overcomes the limitations and problems of the prior art, none, insofar as is known, has been proposed or developed. Accordingly, it is an object of the present invention to provide an electrode system which is relatively simple to manufacture and to use, which is effective at delivering high currents and voltages for use in cardiac defibrillation, which is stable and has a long shelf life, and which permits periodic testing of electrode viability and/or functionality without degrading electrode quality and provides for the ready releasability of the electrodes when the electrodes are removed from the package for use on a patient.

SUMMARY OF THE INVENTION

The present invention substantially meets the aforementioned needs by providing a prepackaged electrode system that has facing gel layers of two electrodes. A conductive layer is interposed between the facing gel layers. The conductive layer has opposing surfaces that the each of the gel layers will adhere to, but are readily releasable from. At the same time, the conductive layer provides a conductive path between the two facing gel layers.

Packaged medical electrodes of the present invention is provided for use with an electromedical device and includes a first electrode having a base layer, a gel layer disposed on the base layer, and a conductive connector communicatively coupled to the gel layer. A second electrode has a base layer, a gel layer disposed on the base layer, and at least one conductive connector communicatively coupled to the gel layer. The gel layers of the first and second electrodes are disposed in a facing relationship and have a liner interposed therebetween, the liner physically separates the gel layers of the first and second electrodes and conductively couples the gel layers of the first and second electrodes. A package encloses the first and second electrodes.

These and other benefits of this invention will become clear from the following description by reference to the drawings.

BRIEF DESCRIPTION OF THE DRAWINGS

FIG. 1 is a top view of one embodiment of the medical electrode system of the present invention;

FIG. 2 is a side view, partially in cross section, of the electrode of FIG. 1, and further showing a test apparatus therefor;

FIG. 3 is a top view of another embodiment of the electrode;

FIG. 4 is a side view of the electrode shown in FIG. 3;

FIG. 5 is a top view of another embodiment of the electrode;

FIG. 6 is a side view of the electrode shown in FIG. 5;

FIG. 7 is a top view of another embodiment of the electrode;

FIG. 8 is a side view of the electrode shown in FIG. 7;

DESCRIPTION OF THE PREFERRED EMBODIMENT

Figure 9:
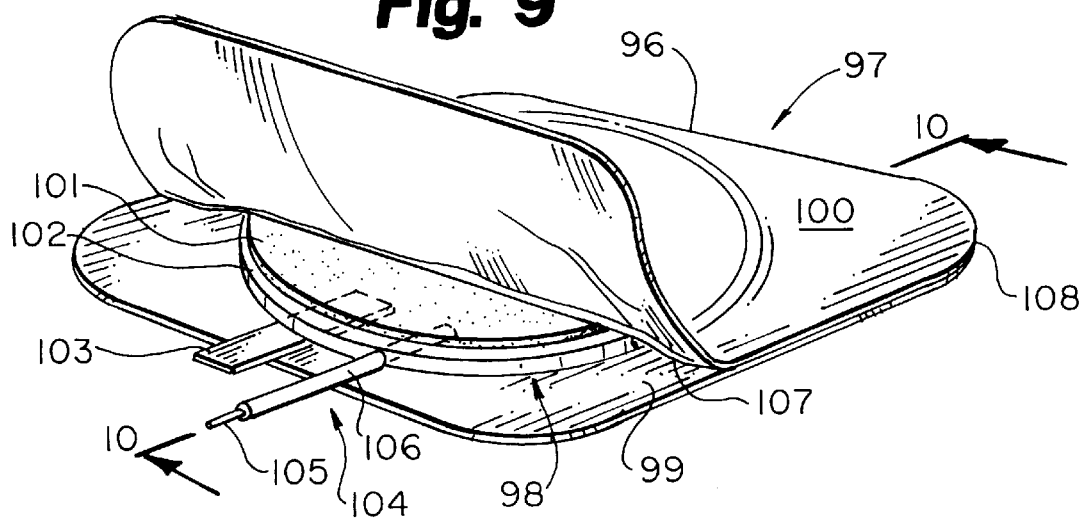
FIG. 9 is a top view of another embodiment of electrode.

The present invention provides an electrode system for use in the medical arts, particularly in cardiac defibrillation. The system includes cooperating electrode embodiments, packaging embodiments and test instrumentation. The system provides convenient, secure and sterile storage means for electrodes which are easy to manufacture and use. The system also provides a means of periodically testing the operability of the stored electrodes without destroying the packaging or electrode, and without compromising the sterility of the materials. The teachings of this invention are applicable to electrodes used for either or both transmitting or receiving, although they are particularly beneficial for use in electrodes used in cardiac defibrillation, which electrodes require transfer of particularly high currents and voltages and a high confidence that the packaged electrodes are in a state of readiness for use after long periods of storage.

Referring to FIGS. 1 and 2 an embodiment of the packaged electrode system 10 is shown to comprise an electrode 11 and a package or enclosure 12. Also shown in FIG. 2 is a test apparatus 13. The electrode 11 is shown to comprise a non-conductive base or backing layer 14, a conductor or conductive layer 15, a lead 16, and a conductive contact layer 17. The base layer 14 is preferably constructed of a thin, flexible polymeric substance such as a urethane foam, or a polyester or polyolefin laminate which provides structural base and insulative properties. The base layer 14 is shown to have a surface area which is substantially coextensive with the surface of the contact layer 17. Alternatively the base layer 14 may be slightly larger than the contact layer 17. In such larger configurations, the base layer 14 may have a pressure sensitive adhesive disposed peripheral to the contact layer 17 on the patient contact side for increased adhesion to the patient's body.

The conductive layer 15 is shown to be disposed on the first or patient side of base layer 14. The conductive layer 15 functions to transfer (disperse) current or voltage from the lead 16 (or to the lead 16 when the electrode 11 is employed in a sensing application) to the patient contact layer 17. Although the conductive layer 15 is shown to have a surface area which is smaller than that of the base layer 14 or contact layer 17, it may alternatively have a dimension which is larger than that shown, or even one which is coextensive with the base layer 14 and contact layer 17. The conductive layer 15 is preferably a homogeneous, solid, thinly deposited metallic substance, or a conductive ink material. Alternatively, the conductive layer 15 may be formed of a flexible mesh material, a conductive adhesive or a deposited ink pattern. Flexible conductive ink compounds known in the art have a conductive filler of gold, silver, aluminum or other conductive materials.

The lead 16 is preferably an insulated wire conductor which extends from a mating point with the conductive layer 15, through the base layer 14, and then has a freely movable end. Various alternatives of this lead 16 design exist and are useable consistent with the general teachings of the invention, including but not limited to uninsulated wire conductors and conductive strips or traces deposited between the contact layer 17 and the base 14 or conductive layers 15. Such a trace of strip may also extend just beyond the base layer 14 for connection with an ancillary connection means such as a wiring harness including conductive clip means.

The conductive contact layer 17 is preferably a thin layer of semi-liquid gel material. The gel maintains direct electrical contact with the skin of the patient to reduce variations in conductance. The gel permits such contact for long periods of time. The gel is a conductive, gelatinous compound which is also flexible for contoured adhesion to the body of a patient. The gel also preferably has a pressure sensitive, moisture resistant adhesive property. Compounds having these characteristics have been developed by Minnesota Mining and Manufacturing, Medtronic, and Lec Tec (Synkara™), Corporations, all of Minnesota, U.S.A. Generally, these compounds have low electrical resistance. The contact layer 17 is for direct contact with the patient's body to transfer current or voltage thereto or therefrom. Overall, although the electrode 11 and its constituent elements are shown to have circular configurations, they may alternatively be formed in various other shapes such as rectangular or square patches.

Figure 18:
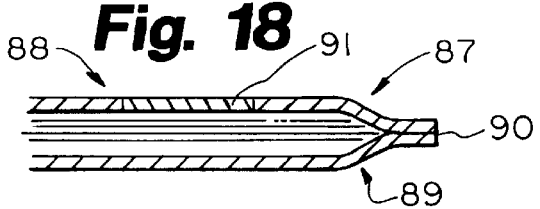
FIG. 18 is a cross-sectional view of packaging material layers.

The package structure 12 is shown to have an envelope-like structure formed of a substantially continuous thin, homogeneous layer 18 of a polymeric, preferably substantially non-gas permeable, material. Alternatively, a shown in FIG. 18, the package 87 embodiment may have a pouch-like structure formed of a pair of thin, flat homogeneous layers 88 and 89 which are sealed or otherwise merged together at their peripheries or outer edges 90. A pair of spaced apart conductive connectors 91 (only one being shown) are formed unitary with layer 88 for electrical contact with contact layer 17. Although the package 12 is shown to have a rectangular configuration various other configurations and shapes are also useable consistent with the invention.

Figure 15:
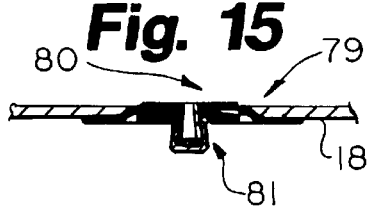
FIG. 15 is a detailed view of a snap-type connection.
Figure 16:
FIG. 16 is a detailed view of a top member of the snap connection shown in FIG. 15.

The package 12 further comprises a pair of conductive connectors 19 and 20 which are separated a predetermined distance from one another for contact with separate areas of the contact layer 17 of the enclosed electrode 11. The connectors 19 and 20 are conductive areas which are shown to have a unitary construction with the package layer 18. The connectors 19 and 20 may alternatively be formed of thin layer strips of conductive material, or a printed conductive ink, disposed on the interior side of the package layer 18, extending from contact nodes on the interior of package layer 18 to peripheral contact areas on the exterior of the package 18. Yet another snap-type embodiment 79 is shown in FIGS. 15 and 16 including a connective member 80 disposed on one side of the base layer 18, and a current dispersion member 81 disposed on the opposite side and being connected to the upper member 80 via an aperture in the base 18. The upper member 80 is shown to have a base 82 and a mating notch 83 for coupling the lower member 81.

Figure 17:
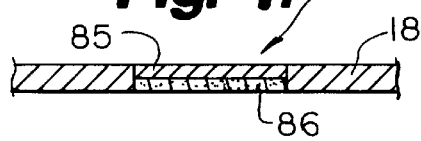
FIG. 17 is a cross-sectional view of a resistive layer.

Referring to FIG. 2, the system 10 of the present invention also comprises a test apparatus 13. The test apparatus 13 includes a current source 23, preferably a battery, test circuitry 24, preferably including measurement components and status indication components such as an analog meter, LCD digital display or light emitting diodes, and connectors 21 and 22 for coupling with the package 12 connectors 19 and 20. In use, the test apparatus 13 is connected to the package connectors 19 and 20. The test circuitry 24 is then activated to form a closed current loop to determine whether continuity exists with respect to the enclosed electrode 11, thereby indicating whether the electrode 11 is still functional. Additionally, a load 85a formed of for example a conductive and semi-conductive material layers 85 and 86, may be added to the current loop as for example is shown in FIG. 17, for purposes of measuring the magnitude of current flow for more precise measurement of electrode 11 condition.

In the case of the electrode system embodiment 10, a current loop is formed including the connector 19, the gel of the contact layer 17 (along a substantially horizontal plane), and the connector 20 which is located at a remote location on the contact layer 14 with respect to the connector 19. Current conducts easily in fresh, semi-liquid gel of the contact layer 17. In contrast, no current conducts, or current conduction is attenuated, in stale, dried gel. This is indicative of the need to dispose of the stored electrode without using it. And, this condition is determinable without the need to open the package 12 and thereby risk compromising the freshness or sterility of a viable electrode 11.

Referring to FIGS. 3 and 4, another embodiment of the packaged electrode system 30 is shown to comprise an electrode 31 and a package or enclosure 32. The electrode 31 is shown to comprise a non-conductive base layer 33, and a conductive gel layer 36. A conductive snap-type connector 40 having a connection member 35 disposed on one side and a current dispersion member 34 disposed on the second side is also shown. The package 32 is shown to have at least one body layer 37 with a pair of contacts 38 and 39 disposed at predetermined locations to electrically connect with the gel layer 36 and connection member 35. In a test mode, a current loop is formed between the contact 39, gel layer 36, current dispersion member 34 and connection member 35 and connector 38.

Referring to FIGS. 5 and 6, another embodiment of the packaged electrode system 45 is shown to comprise an electrode 46 and an enclosure 47. The electrode 46 is shown to comprise a non-conductive base layer 48, a conductive gel layer 55, and a pair of separate conductive layers 49 and 50, each of which are shown to have a lead 51 and 52 extending therefrom and terminating in a connective node 53 and 54. The lead pair 51 and 52 (and layer pair 49 and 50) provide a redundant circuit path for increased reliability of use in emergency settings. The package 47 is shown to have at least one body layer 56 with a pair of contacts 57 and 58 disposed at predetermined locations to electrically couple with connective nodes 53 and 54. In a test mode, a current loop is formed between a contacts 57 or 58, it's respective connective node 53 or 54 and lead 51 or 52, and its respective conductive layer 49 or 50. In a properly functioning electrode 46, current conducts through the gel 55 from one conductive layer 49 to the other 50, and then back to the test apparatus through the above-mentioned path.

Referring to FIGS. 7 and 8, another embodiment of the packaged electrode system 64 is shown to comprise an electrode 65 and a unitary package 66. The electrode 65 is shown to comprise a non-conductive base layer 67, and a conductive gel layer 70. A snap-type connector with members 68 and 69 is electrically coupled to the gel layer 70.

The package 66 is shown to have at least one body layer 71 which is coupled to the electrode base layer 67 at tear-away perforated lines 73. A connector 72 is shown in FIG. 8 disposed for contact with the electrode gel layer 70. In a test mode, a current loop is formed between the connector 72, the gel layer 70, and the snap-type connector members 68 and 69.

Figure 10:
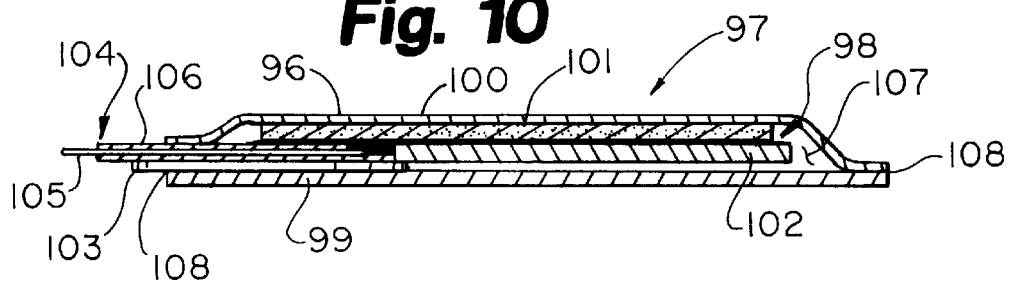
FIG. 10 is a side view of the electrode shown in FIG. 9.

Referring to FIGS. 9 and 10, another embodiment of the packaged electrode system 97 is shown to comprise an electrode 98 and a package 96. The electrode 98 is shown to comprise a non-conductive base layer 101, a conductive gel layer 102, and a lead 104 having a conductor 105 and an insulator 106, which is shown to be embedded directly in the gel layer 102. Alternatively, the lead 104 may be connected to a conductive current dispersion layer (not shown). A conductive test strip 103 is also shown to be adhered to the surface of the gel 102 at a location remote from the lead 104 for test purposes. Test strip 103 is bonded to package layer 99 and is designed to release from the gel 102 upon removal of the package layer 99.

The package 96 is shown to have a pair of layers 99 and 100 which overlap to form an interior cavity 107 and are sealingly connected at their peripheries 108. In a test mode, a current loop is formed between the lead 104, the gel layer 102 and the test strip 103. The test strip 103 and the lead 104 are shown extended through the package periphery 108 for contact with an external test apparatus.

Figure 11:
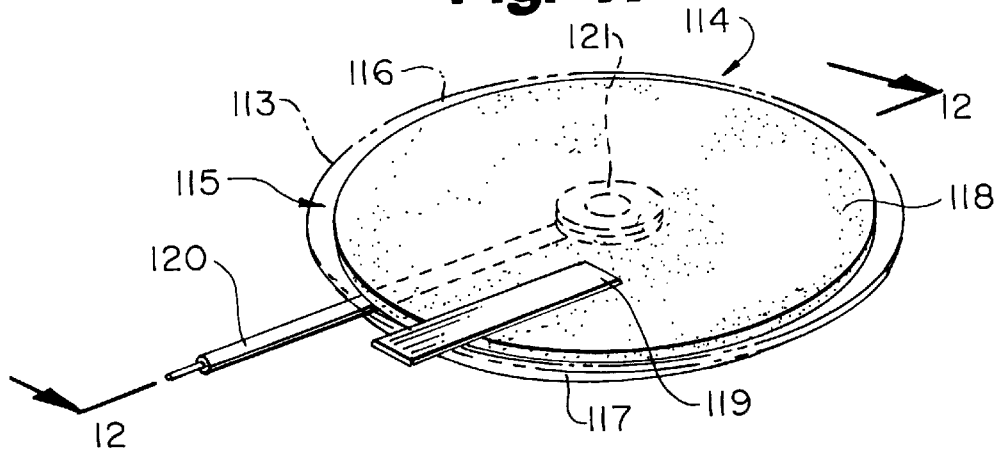
FIG. 11 is a top view of another embodiment of the electrode.
Figure 12:
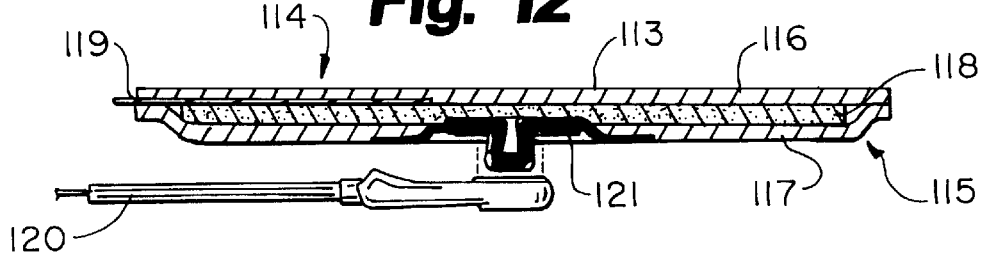
FIG. 12 is a side view of the electrode shown in FIG. 11.

Referring to FIGS. 11 and 12, another embodiment of the packaged electrode system 114 is shown to comprise an electrode 115 and an enclosure 113. The electrode 115 is shown to comprise a non-conductive base layer 117, and a conductive adhesive gel layer 118 which is connected to a snap-type connection node 121 or the like, and an associated lead 120. The package 113 is shown to comprise a single top layer of non-conductive material 116 which is laminated or adhesively mated to the periphery of the electrode base layer 117. In use, the gel layer 118 is releasable from the package layer 116. A test strip 119 is disposed on the interior of the package 113, adhesively connected to the gel layer 118, and extending to the package exterior. In a test mode, a current loop is formed between the lead 120, node 121, gel layer 118 and the test strip 119.

Figure 13:
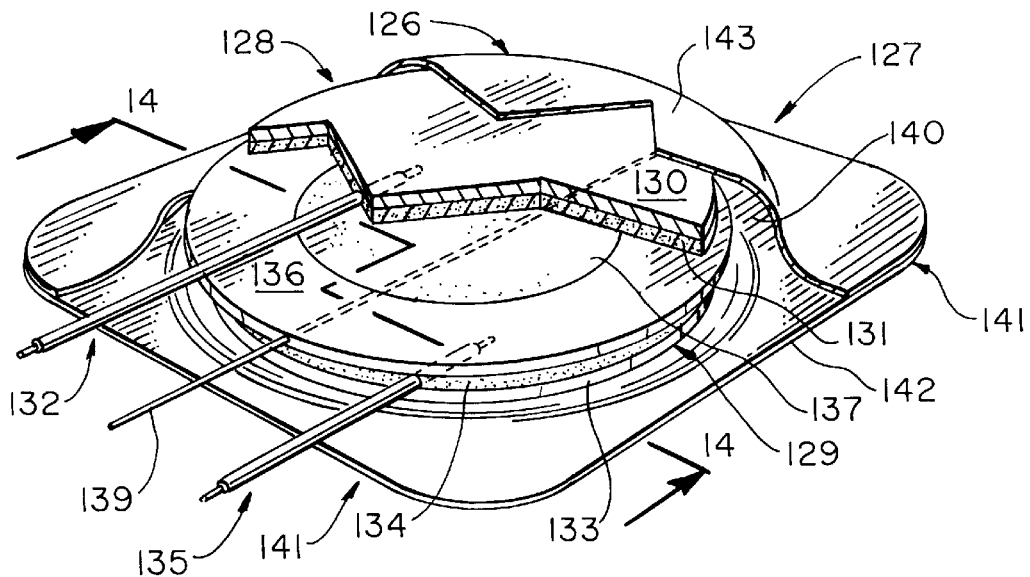
FIG. 13 is a top view of another embodiment of the electrode.
Figure 14:
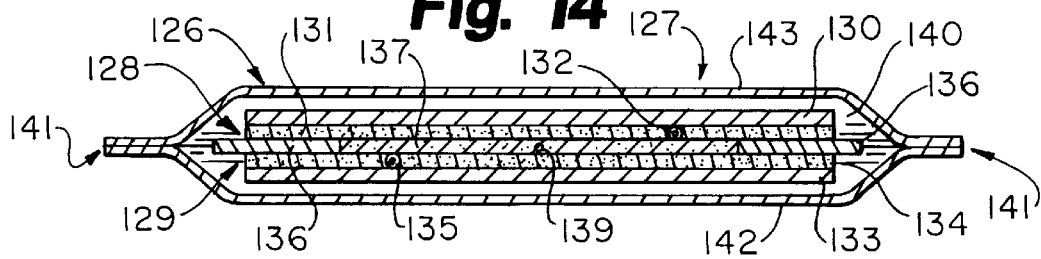
FIG. 14 is a side view of the electrode shown in FIG. 13.

Referring to FIGS. 13 and 14, another embodiment of the packaged electrode system 127 is shown to comprise a pair of electrodes 128 and 129 and a package 126. The electrodes 128 and 129 are shown to comprise non-conductive base layers 130 and 133, and conductive gel layers 131 and 134. Leads 132 and 135 extend from the respective gel layers 131 and 134. The package 126 is shown to have a pair of overlapping layers 142 and 143 which are sealed at their peripheries 141 to form an enclosure 140 housing the electrodes 128 and 129. Importantly, the electrodes 128 and 129 are oriented with their respective gel layers 131 and 134 mating with a resistive layer 137 (and an optional separator layer 136) formed of a conductive/resistive material as known in the art. A conductive lead 139 or strip extends from the resistive layer through the package periphery 141, as do the electrode leads 132 and 135.

In a test mode, a current loop is formed between, for example, a lead 132, the gel layer 131, the resistive layer 137, and the remaining gel layer 134 and lead 135. The circuit can be altered to include the lead 139.

Figure 19:
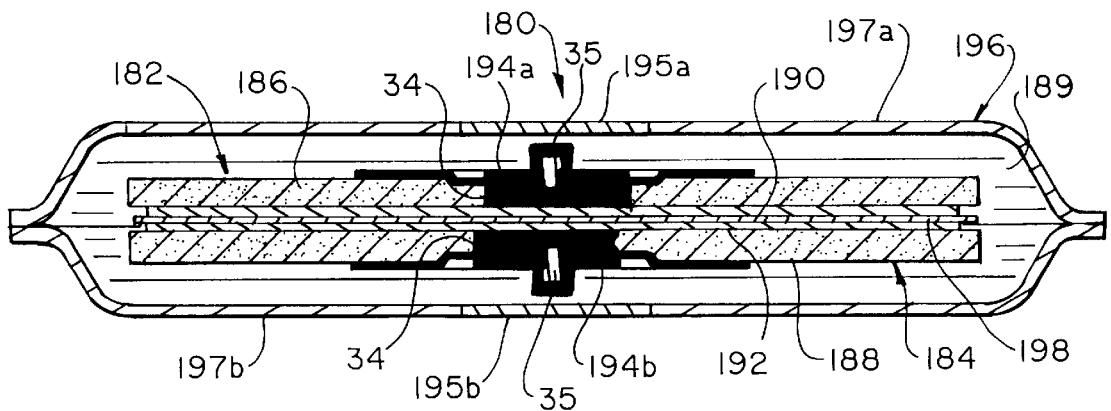
FIG. 19 is a cross-sectional view of another embodiment having snap connectors and a conductive liner.

FIG. 19 depicts a further embodiment of the present invention. A packaged electrode system is shown generally at 180. The packaged electrode system 180 includes a first electrode 182, a second electrode 184, and an enclosing package 196.

The package 196 is formed of package portion 197a, 197b, bonded at the peripheries thereof to define an enclosure 189. In a preferred embodiment, a conductive polymeric liner 198 is disposed between the electrodes 182, 184. Each of the electrodes 182, 184 has a nonconductive base 186, 188, respectively. A respective conductive gel layer 190, 192 is operably coupled to the nonconductive base 186, 188.

Snap connectors 194a, 194b are operably coupled to the nonconductive bases 186, 18 and communicatively coupled to the conductive gel layers 190, 192. As previously described in reference to FIGS. 3 and 4, the snap connectors 194a, 194b each have a connection member 35 disposed on one side of the respective nonconductive bases 186, 18 and a current dispersion member 34 that is communicatively coupled to the conducting gel layers 190, 192.

Contacts 195a, 195b are preferably formed unitary with the respective package portion 197a, 197b and are disposed proximate the snap connectors 194a, 194b. The contacts 195a, 195b are normally positioned spaced apart from the snap connectors 194a, 194b. The spacing electrically isolates the contacts 195a, 195b and snap connectors 194a, 194b. Depressing the contacts 195a, 195b causes the contacts 195a, 195b to come into physical and electrical contact with the snap connectors 194a, 194b.

The packaged electrode system 180 may additionally have an associated lead coupled to each of the snap connectors 194a, 194b. Such a lead is similar to the associated lead 120, previously described in reference to FIGS. 11 and 12, coupled to the connection member 35 of each of the snap connectors 194a, 194b. The use of such associated leads 120 negates the need for contacts 195a, 195b. The associate lead preferably carries through an aperture defined in the package 196, for connection external to the package 196, as desired.

The electrodes 182, 184 are disposed within the enclosure 189 formed by the package 196 with the respective conductive gel layers 190, 192 in a facing relationship. The conductive liner 198 is interposed between the conductive gel layers 190 and 192. The conductive liner 198 physically separates the conductive gel layers 190, 192 and communicatively couples conductive gel layers 190, 192. The conductive gel layers 190 192 are readily releasable from the conductive liner 198.

Preferably, the conductive polymeric liner 198 is inherently conductive by the nature of its structure. Such inherently conductive structure includes alternating double or triple bonded polymers. Alternatively, the conductive polymeric liner 198 may not be inherently conductive but may be doped or filled with conductive particles such as graphite, carbon black, and metal powder in order to provide conductivity.

Examples of doped or filled conductive polymers suitable to form the conductive polymeric liner 198 include:

1. doped polyethylene (PE);
2. doped polyethylene terephthalate (pET);
3. doped polytetrafluoroethylene (pTFE); and
4. doped polyfluorinated ethylene propylene (pFEP).

The family of polymers known as polyfluorinated hydrocarbons are of particular interest for use in forming the conductive polymeric liner 198 because of their exhibited low adhesion properties. Of the members of this family, the polyfluorinated ethylene is preferred because this polymer is extrudable, making it easier to form the conductive polymeric liner 198.

Figure 20:
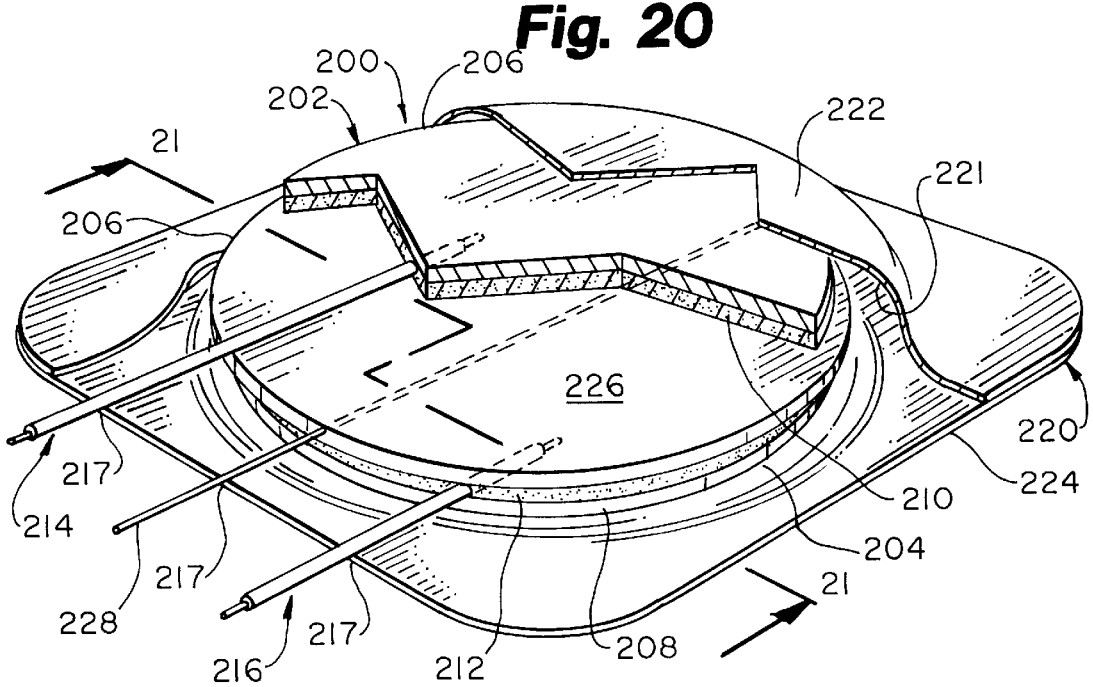
FIG. 20 is a perspective view of another embodiment with a portion of the package broken away.
Figure 21:
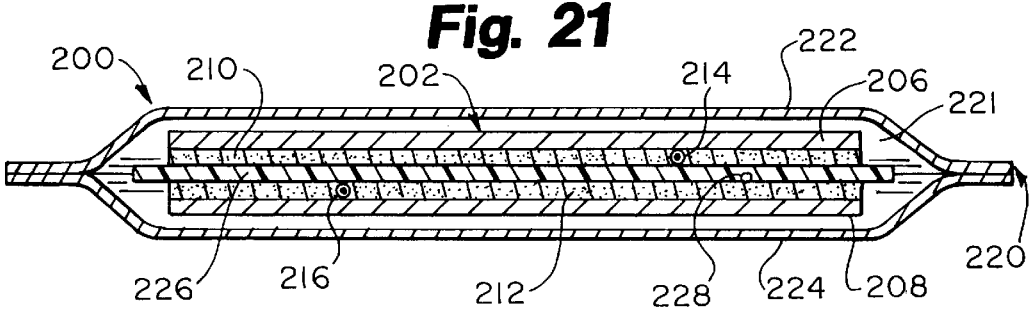
FIG. 21 is a section view of the embodiment of FIG. 20 taken along line 21 thereof.

A further embodiment of the packaged electrode system of the present invention is depicted in FIGS. 20 and 21. A packaged electrode system is shown generally at 200. The packaged electrode system 200 includes a first electrode 202, a second electrode 204, and an enclosing package 220. The electrodes 202, 204 are releasably disposed in an enclosure 221 defined by the package 220. In a preferred embodiment, a conductive polymeric liner 226 is disposed between the electrodes 202, 204.

Each of the electrodes 202, 204 has a nonconductive base 206, 208, respectively. A respective conductive gel layer 210, 212 is operably coupled to the nonconductive base 206, 208.

Leads 214, 216 are communicatively coupled to the conductive gel layers 210, 212. The leads 214, 216 pass through an aperture 217 defined in the periphery of the package 220 for connection to conductors external to the package 220 as desired.

The package 220 has a top package portion 222 and a bottom package portion 224. The package portions 222, 224 are sealed at their peripheries to form the enclosure 221, housing the electrodes 202, 204.

In a preferred embodiment, a conductive polymeric liner 226 is disposed between the electrodes 202, 204. The electrodes 202, 204 are disposed within the enclosure formed by the package 220 with the conductive gel layers 210, 212 in a facing relationship. The liner 226 is interposed between the conductive gel layers 210 and 212. The liner 226 both physically separates the conductive gel layers 210, 212 and communicatively couples conductive gel layers 210, 212.

Lead 228 is communicatively coupled to the conductive polymeric liner 226. The lead 228 passes through the aperture 217 defined in the periphery of the package 220 for connection to conductors external to the package 220 as desired.

Preferably, the conductive polymeric liner 226 is inherently conductive by the nature of its structure and is substantially identical to the conductive polymeric liner 198 described in conjunction with FIG. 19 above.

As many changes are possible to the embodiments of this invention utilizing the teachings thereof, the descriptions above, and the accompanying drawings should be interpreted in the illustrative and not the limited sense.

That which is claimed is:

1. Packaged medical electrodes for use with an electromedical device comprising:
   a first electrode having;
      a base layer;
      a gel layer disposed on the base layer;
      a conductive connector communicatively coupled to the gel layer;
   a second electrode having;
      a base layer;
      a gel layer disposed on the base layer;
      at least one conductive connector communicatively coupled to the gel layer;
      the gel layers of the first and second electrodes being disposed in a facing relationship and having a liner interposed therebetween, the liner physically separating the gel layers of the first and second electrodes and conductively coupling the gel layers of the first and second electrodes; and
   a package enclosing the first and second electrodes.

2. The packaged electrodes of claim 1 further including at least two conductive devices, a first conductive device being communicatively coupled to the gel layer of the first electrode and a second conductive device being communicatively coupled to being communicatively coupled to the gel layer of the second electrode, the conductive devices being selected from a group consisting of:
   wire leads; and
   snap connectors.

3. The packaged electrodes of claim 2 wherein the liner is a conductive polymer.

4. The packaged electrodes of claim 3 wherein the liner is selected from a group consisting of:
   an inherently conductive polymer; and
   a doped polymer.

5. The packaged electrodes of claim 4 wherein the liner is an inherently conductive polymer having a structure comprised of alternating double bonds.

6. The packaged electrodes of claim 4 wherein the liner is an inherently conductive polymer having a structure comprised of alternating triple bonds.

7. The packaged electrodes of claim 4 wherein the liner is a doped polymer having a dopant being selected from a group consisting of:
   graphite;
   carbon black; and
   metal powder.

8. The packaged electrodes of claim 4 wherein the liner is a doped polymer selected from a group consisting of:
   doped polyethylene;
   doped polyethylene terephthalate;
   doped polytetrafluoroethylene; and
   doped polyfluorinated ethylene propylene.

9. The packaged electrodes of claim 4 wherein the liner is a doped polymer that exhibits low adhesion properties.

10. The packaged electrodes of claim 9 wherein the liner is a doped polymer that is a polyfluorinated hydrocarbon.

11. The packaged electrodes of claim 10 wherein the liner is a doped polymer that is extrudable.

12. The packaged electrodes of claim 11 wherein the liner is a doped polymer that is formed of polyfluorinated ethylene propylene.

13. The packaged electrodes of claim 2 wherein the gel layer is a conductive, semi-liquid gel layer disposed on a first side of a base layer.

14. The packaged electrode as in claim 2 further including:
- first and second conductive connectors disposed at predetermined locations with respect to the first electrode wherein the first conductive connectors is electrically connected to the gel layer thereof and the second conductive connectors is electrically connected to a snap type connector; and
- first and second conductive connectors disposed at predetermined locations with respect to the second electrode wherein the first conductive connectors is electrically connected to the gel layer thereof and the second conductive connectors is electrically connected to a snap type connector.

15. The packaged electrodes as in claim 14 wherein each of the two the snap type connectors has a connection member adapted for connection to an electrical lead and a current dispersion member in contact with the gel layer.

16. The packaged electrodes as in claim 2 wherein the package encompasses the base layer, the gel layer and a snap type connector of each of the first and second electrodes.

17. The packaged electrodes as in claim 14 wherein a portion of each of the snap type connectors protrudes through an aperture defined in the package.

18. Sealed package medical electrodes for use with an electromedical device comprising:
- a first electrode, having;
- a nonconductive base layer having a first and second side;
- a conductive gel layer disposed on the first side of the base layer;
- a snap type connector mounted to the base layer wherein the snap type connector has a connection member projecting through the base layer and a current dispersion layer in contact with the gel layer;
- a second electrode, having;
- a nonconductive base layer having a first and second side;
- a conductive gel layer disposed on the first side of the base layer;
- a snap type connector mounted to the base layer wherein the snap type connector has a connection member projecting through the base layer and a current dispersion layer in contact with the gel layer; and
- an envelope arranged to form an interior cavity wherein the current dispersion member of the first and second electrodes lies in the interior cavity and the connection member of the first and second electrodes projects from the interior to a point exterior the envelope.

19. The sealed package medical electrodes of claim 18 wherein the gel layers of the first and second electrodes are disposed in a facing relationship and further including a liner interposed between the gel layers of the first and second electrodes, the liner physically separating the gel layers of the first and second electrodes and conductively coupling the gel layers of the first and second electrodes.

20. The sealed package medical electrodes of claim 18 further including a lead electrically connected to the snap type connectors of the first and second electrodes.

21. The sealed package medical electrodes of claim 20 further comprising a test lead electrically connected to the liner and extending outside of the interior cavity.

22. The sealed package medical electrodes of claim 21 wherein the lead is configured to receive the connection member of the snap type connector of the first and second electrodes.

23. The sealed package medical electrodes of claim 19 wherein the liner is a conductive polymer.

24. The sealed package medical electrodes of claim 23 wherein the liner is selected from a group consisting of:
- an inherently conductive polymer; and
- a doped polymer.

25. The sealed package medical electrodes of claim 24 wherein the liner is an inherently conductive polymer having a structure comprised of alternating double bonds.

26. The sealed package medical electrodes of claim 24 wherein the liner is an inherently conductive polymer having a structure comprised of alternating triple bonds.

27. The sealed package medical electrodes of claim 24 wherein the liner is a doped polymer having a dopant being selected from a group consisting of:
- graphite;
- carbon black; and
- metal powder.

28. The sealed package medical electrodes of claim 24 wherein the liner is a doped polymer selected from a group consisting of:
- doped polyethylene;
- doped polyethylene terephthalate;
- doped polytetrafluoroethylene; and
- doped polyfluorinated ethylene propylene.

29. The sealed package medical electrodes of claim 24 wherein the liner is a doped polymer that exhibits low adhesion properties.

30. The sealed package medical electrodes of claim 29 wherein the liner is a doped polymer that is a polyfluorinated hydrocarbon.

31. The sealed package medical electrodes of claim 30 wherein the liner is a doped polymer that is extrudable.

32. The sealed package medical electrodes of claim 31 wherein the liner is a doped polymer that is formed of polyfluorinated ethylene propylene.

* * * * *

UNITED STATES PATENT AND TRADEMARK OFFICE
Certificate

Patent No. 5,984,102

Patented: November 16, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Sew-Wah Tay, Plymouth, MN; Byron L. Gilman, Plymouth, MN; and Karl J. F. Kroll, Maple Grove, MN.

Signed and Sealed this Twenty-eighth Day of December 2004.

MICKEY YU
*Supervisory Patent Examiner*
Art Unit 3728